US00RE35919E

United States Patent [19]

Yamashita et al.

[11] E Patent Number: Re. 35,919

[45] Reissued Date of Patent: Oct. 13, 1998

[54] PROCESS FOR SEPARATING OPTICAL ISOMERS

[75] Inventors: Akira Yamashita; Fumihiko Shoji, both of Hyogo, Japan

[73] Assignee: Daicel Chemical Industries, Ltd., Tokyo, Japan

[21] Appl. No.: 911,680

[22] PCT Filed: Feb. 20, 1991

[86] PCT No.: PCT/JP91/00213

§ 371 Date: Aug. 21, 1991

§ 102(e) Date: Aug. 21, 1991

[87] PCT Pub. No.: WO91/13046

PCT Pub. Date: Sep. 5, 1991

Related U.S. Patent Documents

Reissue of:

[64] Patent No.: 5,126,055
Issued: Jun. 30, 1992
Appl. No.: 752,663
Filed: Aug. 21, 1991

U.S. Applications:

[63] Continuation of Ser. No. 516,844, Aug. 18, 1995.

[30] Foreign Application Priority Data

Feb. 23, 1990 [JP] Japan ..... 2-44139
Jan. 22, 1991 [JP] Japan ..... 3-5669

[51] Int. Cl.[6] ..... B01D 15/08

[52] U.S. Cl. ..... 210/659; 210/198.2

[58] Field of Search ..... 210/635, 656, 210/659, 198.2; 435/280

[56] References Cited

U.S. PATENT DOCUMENTS

| | | | |
|---|---|---|---|
| 2,985,589 | 5/1961 | Broughton et al. | 210/34 |
| 4,042,327 | 8/1977 | Haney | 210/635 |
| 4,335,226 | 6/1982 | Muller | 210/656 |

(List continued on next page.)

FOREIGN PATENT DOCUMENTS

| | | | |
|---|---|---|---|
| 2 593 409 | 7/1987 | France | 210/198.2 |
| 58-20208 | 2/1983 | Japan | 210/198.2 |
| 64-85106 | 3/1989 | Japan | 210/198.2 |
| 1163654 | 6/1989 | Japan | 210/198.2 |
| 1199643 | 8/1989 | Japan | 210/198.2 |
| 1202658 | 8/1989 | Japan | 210/198.2 |
| 1216943 | 8/1989 | Japan | 210/198.2 |
| 2167052 | 5/1986 | United Kingdom | 210/198.2 |

OTHER PUBLICATIONS

Hawley's Condensed Chemical Dictionary, Eleventh Edition, New York, Van Nostrand Reinhold, 1987, p. 276.

Snyder, Introduction to Modern Liquid Chromatography, John Wiley & Sons, Inc., 1979, pp. 177–183.

Industrial Chemist, "Process–scale liquid chromatography", Mark. D. Weiss, Aug. 1987, pp. 16–20.

UOP Sorbex Processes, "UOP Sorbex Separations Technology", Nikki Universal Co., Ltd., Oct. 1989, 8 pages.

*Primary Examiner*—Ernest G. Therkorn

*Attorney, Agent, or Firm*—Flynn, Thiel, Boutell & Tanis, P.C.

[57] ABSTRACT

A process for separating optical isomers in a simulated moving bed system, which comprises introducing a solution containing an optical isomer mixture and a desorbing liquid into a packed bed containing an optical resolution packing therein and having front and rear ends thereof connected to each other endlessly via a fluid passage to circulate a fluid unidirectionally and at the same time drawing out a solution containing one of the separated isomers and another solution containing the other isomer from the packed bed, wherein a port 13 for introducing a desorbing liquid, a port 14 for drawing out a solution containing a strongly adsorbable optical isomer, i.e. an extract, a port 15 for introducing a solution containing a mixture of optical isomers, and a port 16 for drawing out a solution containing a weakly adsorbable optical isomer, i.e. a raffinate, are arranged in the packed bed in this order along the direction of fluid flow and the positions of these ports are successively moved in the direction of fluid flow in the packed bed intermittently.

14 Claims, 1 Drawing Sheet

U.S. PATENT DOCUMENTS

| | | | |
|---|---|---|---|
| 4,381,399 | 4/1983 | Olsen | 210/659 |
| 4,402,832 | 9/1983 | Gerhold | 210/659 |
| 4,416,784 | 11/1983 | Nakao | 210/635 |
| 4,512,898 | 4/1985 | Oi | 210/656 |
| 4,539,399 | 9/1985 | Armstrong | 210/502.1 |
| 4,549,965 | 10/1985 | Davis | 210/635 |
| 4,765,903 | 8/1988 | D'Andrea | 210/635 |
| 4,781,858 | 11/1988 | Mizukami | 210/635 |
| 4,816,445 | 3/1989 | Mitsuhashi | 127/30 |
| 4,818,394 | 4/1989 | Okamoto | 210/198.2 |
| 4,842,935 | 6/1989 | Shinbo et al. | 210/198.2 |
| 4,919,803 | 4/1990 | Doyle | 210/198.2 |
| 4,960,762 | 10/1990 | Sellergren | 210/656 |
| 5,032,277 | 7/1991 | Okamoto et al. | 210/635 |
| 5,104,543 | 4/1992 | Brandt | 210/635 |

PROCESS FOR SEPARATING OPTICAL ISOMERS

Matter enclosed in heavy brackets [ ] appears in the original patent but forms no part of this reissue specification; matter printed in italics indicates the additions made by reissue.

*This application is a reissue continuation of U.S. Ser. No. 08/516,844, filed Aug. 18, 1995, now abandoned, which is a reissue application of U.S. Pat. No. 5,126,055, issued Aug. 21, 1991.*

INDUSTRIAL APPLICABILITY

The present invention relates to a novel process for separating optical isomers.

BACKGROUND ART

As well known in the art, optical isomers generally have different activities to living bodies, even though they are chemically the same compounds. Accordingly, in the fields of pharmaceuticals, pharmaceutical manufacture and biochemistry-related industries, it is an extremely important task to prepare optically pure compounds in order to improve the efficacy of pharmaceuticals per unit dose and to avoid the side effects and damages caused by pharmaceuticals. The separation of an optical isomer mixture, that is, optical resolution, has been performed according to the diastereomer method, the crystallization method, the enzyme method and the separating membrane method. In these methods, however, the types of compounds for which optical resolution is feasible are often limited, so that they are not suitable for general purposes. Although chromatography is available for such separation, currently known chromatographic methods are of batch type, so that noncontinuous and nonsteady operations are inevitable and hence they are not suitable for the separation in a large quantity. In addition, a large quantity of an eluent is needed to and the concentration of the desired compound in an eluate is extremely low, so that there has been a drawback that much energy and complicated process are required for recovery. Therefore, the development of a method capable of efficient separation in a large quantity has been desired in the art.

DISCLOSURE OF THE INVENTION

The present invention provides a novel process capable of efficiently separating an optical isomer. The present inventors have made extensive studies to find out that efficient separation of an optical isomer in a large quantity can be performed by the use of a simulated moving bed system, which has led to the completion of the present invention.

Accordingly, the present invention relates to a process for separating optical isomers in a simulated moving bed system, characterized by introducing a solution containing an optical isomer mixture and a desorbing liquid into a packed bed containing an optical resolution packing therein and having front and rear ends thereof connected to each other endlessly via a fluid passage to circulate a fluid unidirectionally and at the same time drawing out a solution containing one of the separated isomers and another solution containing the other isomer from the packed bed, wherein a port for introducing a desorbing liquid, a port for drawing out a solution containing a strongly adsorbable optical isomer, i.e. an extract, a port for introducing a solution containing an optical isomer mixture, and a port for drawing out a solution containing a weakly adsorbable optical isomer, i.e. a raffinate, are arranged in the packed bed in this order along the direction of fluid flow and the positions of these ports are successively moved in the direction of fluid flow in the packed bed intermittently.

The simulated moving bed system means a system in which ports for introducing a desorbing liquid and ports for drawing out an adsorbate fluid are arranged in a packed bed containing a solid adsorbent therein and having front and rear ends thereof connected to each other via a fluid passage to circulate a fluid, along the direction of fluid flow in the bed, an upstream introduction port and an upstream drawout port being successively changed over by the downstream counterparts at given time intervals, respectively, to thereby separate a feedstock fluid into a component (adsorbate component) which is relatively strongly adsorbed by the solid adsorbent and a component (nonadsorbate component) which is relatively weakly adsorbed by the solid adsorbent. The simulated moving bed system per se is known in the art (see for example, Japanese Patent Publication No. 15681/1967). This simulated moving bed technology has been utilized in, for example, the manufacture of fructose, the separation of maltose and the recovery of coenzyme. However, no prodess for separating optical isomers by the use of a simulated moving bed system is known at all.

Preferred embodiments of the process of the present invention for separating optical isomers using a simulated moving bed system will now be described in greater detail. In the present invention, the packed bed of the simulated moving bed system contains therein a packing, such as a silica gel having carried thereon an optically active high-molecular compound, e.g., a polysaccharide derivative such as esters and carbamates of amylose and cellulose, a polyacrylate derivative and a polyamide derivative, a particulate material prepared from a polymer per se and a silica gel having carried thereon a low-molecular compound having an optical resolution capability, e.g., crown ether and cyclodextrin derivatives, which packing is known as an optical resolution packing. The packed bed has front and rear ends thereof connected to each other endlessly via a fluid passage to circulate a fluid unidirectionally. Introduced into the packed bed are a solution containing an optical isomer mixture and a desorbing liquid comprising an organic solvent, e.g., an alcohol such as methanol or isopropanol, a hydrocarbon such as hexane, and/or an aqueous solution containing a salt such as copper sulfate or a perchlorate salt. At the same time, a solution containing one optical isomer and a solution containing another optical isomer are drawn out of the packed bed. A port for introducing a desorbing liquid, a port for drawing out a solution containing a strongly adsorbable optical isomer, i.e. an extract, a port for introducing a solution containing an optical isomer mixture, and a port for drawing out a solution containing a weakly adsorbable optical isomer, i.e. a raffinate, are arranged in the packed bed in this order along the direction of fluid flow and the positions of these ports are successively moved in the direction of fluid flow in the packed bed intermittently.

In the adsorption and separation by the simulated moving bed system according to the present invention, the following operations of adsorption, concentration, desorption, and desorbing liquid recovery as the basic operations are continuously carried out in circulation.

(1) ADSORPTION

The optical isomer mixture is brought into contact with the packing, so that a strongly adsorbable optical isomer (strongly adsorbable component) is adsorbed while another weakly adsorbable optical isomer (weakly adsorbable component) is recovered as a raffinate flow together with the desorbing liquid.

(2) CONCENTRATION

The packing having the strongly adsorbable component adsorbed thereon is brought into contact with part of the extract described below, so that the weakly adsorbable component remaining on the packing is expelled and the strongly adsorbable component is concentrated.

(3) DESORPTION

The packing containing the concentrated strongly adsorbable component is brought into contact with the desorbing liquid, so that the strongly adsorbable component is expelled from the packing and recovered together with the desorbing liquid as an extract flow.

(4) DESORBING LIQUID RECOVERY

The packing having substantially only the desorbing liquid adsorbed thereon is brought into contact with part of the raffinate flow, so that part of the desorbing liquid contained in the packing is recovered as a desorbing liquid recovery flow.

DESCRIPTION OF THE PREFERRED EMBODIMENTS

Figure 2:
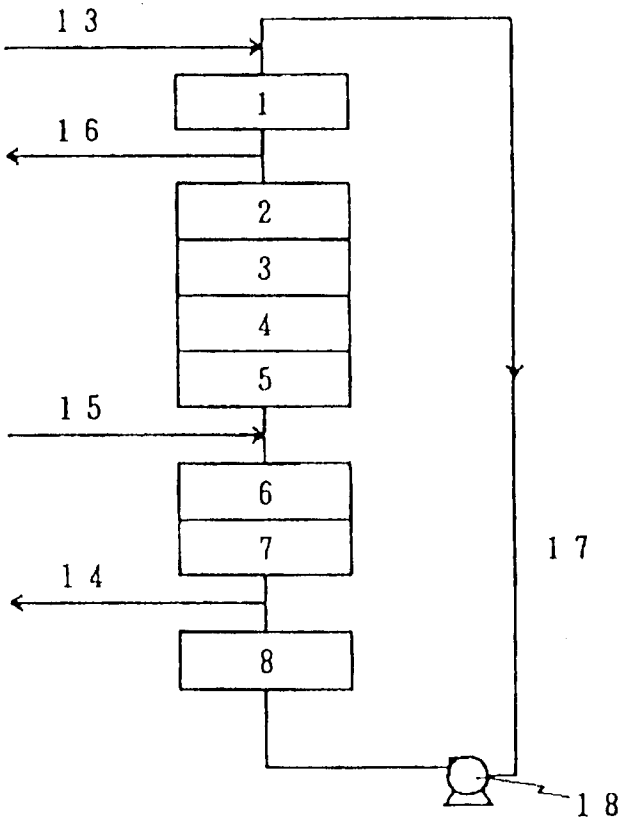
FIG. 2 is a schematic diagram showing another form of the simulated moving bed system to be used in the present invention.

In the drawings,

1–12: adsorbing chamber
13: desorbing liquid feeding line
14: extract draw-out line
15: feeding line for a solution containing an optical isomer
16: raffinate draw-out line
17: recycle line
18: pump.

The process of the present invention will now be described by referring to the drawings.

Figure 1:
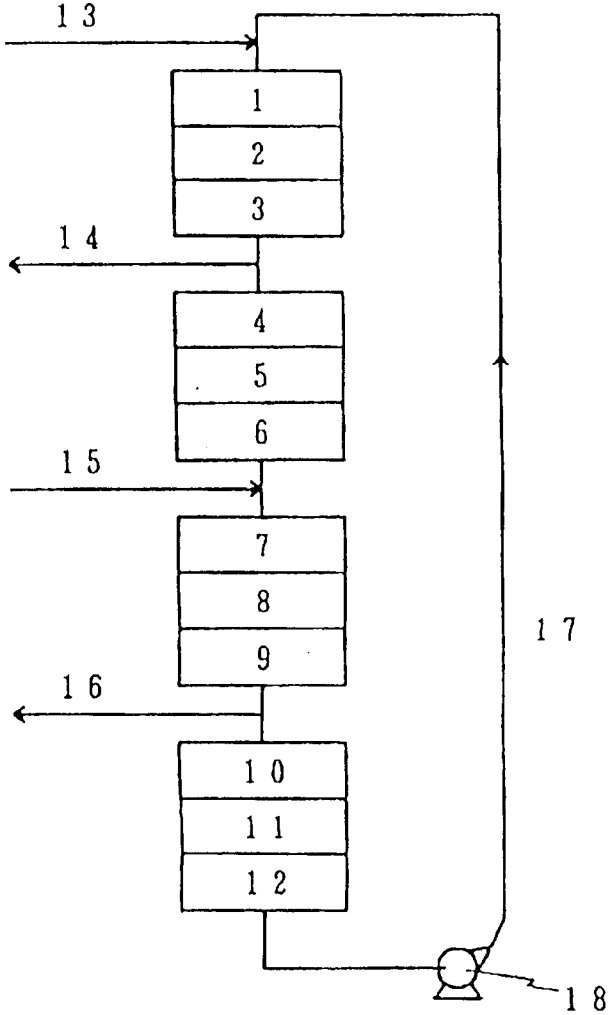
FIG. 1 is a schematic diagram showing one form of the simulated moving bed system to be used in the present invention.

FIG. 1 is a schematic diagram showing one form of the simulated moving bed system to be used in the present invention; and FIG. 2 is a schematic diagram showing another form of the simulated moving bed system to be used in the present invention. In FIG. 1, the inside of the packed bed constituting the principal part of the simulated moving bed is partitioned into 12 packed bed units, while in FIG. 2, it is partitioned into 8 packed bed units. The number and the size of such packed bed units are selected depending on the composition, concentration, flow rate and pressure loss of the solution containing an optical isomer mixture and on the size of the apparatus, and are not particularly limited.

In the drawings, numerals 1 to 12 represent chambers in which a packing is incorporated (adsorbing chamber) and which are connected with one another, numeral 13 represents a desorbing liquid feeding line, numeral 14 represents an extract draw-out line, 15 represents a feeding line for a solution containing an optical isomer, 16 represents a raffinate draw-out line, 17 represents a recycle line, and 18 represents a pump.

In the arrangement of the adsorbing chambers 1 to 12 and the lines 13 to 16 indicated in FIG. 1, desorption is performed in the adsorbing chambers 1 to 3, concentration in the adsorbing chambers 4 to 6, adsorption in the adsorbing chambers 7 to 9, and desorbing liquid recovery in the adsorbing chambers 10 to 12. In such a simulated moving bed system, each of the feeding lines and draw-out lines is moved for a distance corresponding to one adsorbing chamber in the direction of fluid flow by manipulating valves at given time intervals. Accordingly, in the resulting arrangement of the adsorbing chambers, desorption is performed in the adsorbing chambers 2 to 4, concentration in the adsorbing chambers 5 to 7, adsorption in the adsorbing chambers 8 to 10 and desorbing liquid recovery in the adsorbing chambers 11 to 1. By successively performing these operations, the separation of an optical isomer mixture is accomplished continuously and efficiently.

In the arrangement of the adsorbing chambers 1 to 8 and lines 13 to 16 indicated in FIG. 2, desorbing liquid recovery is performed in the adsorbing chamber 1, adsorption in the adsorbing chambers 2 to 5, concentration in the adsorbing chambers 6 to 7, and desorption in the adsorbing chamber 8. In such a simulated moving bed system, each of the feeding lines and draw-out lines is moved for a distance corresponding to one adsorbing chamber in the direction of fluid flow by manipulating valves at given time intervals. Accordingly, in the resulting arrangement of the adsorbing chambers, desorbing liquid recovery is performed in the adsorbing chamber 2, adsorption in the adsorbing chambers 3 to 6, concentration in the adsorbing chambers 7 to 8, and desorption in the adsorbing chamber 1. By successively performing these operations, the separation of an optical isomer mixture is accomplished continuously and efficiently.

EFFECT OF THE INVENTION

The industrial effect of the process of the present invention for separating optical isomers according to a simulated moving bed system is remarkably excellent, because this process allows an optical isomer mixture to be separated continuously and efficiently, works well even with a reduced amount of a desorbing liquid used, and can deal with a large amount of optical isomers.

EXAMPLES

The present invention will now be described in more detail by referring to the following Examples, though it is not limited to these Examples only.

EXAMPLE 1

1,3-Butanediol diacetate was fed at a rate of 6 ml/min (total concentration of isomers: 1000 mg/ml) into a simulated moving bed apparatus comprised of 8 connected columns, as adsorbing chambers, each having a diameter of 2 cm and a length of 50 cm and containing a packing for use in the separation of an optical isomer (Chiralcel OB of 20 μm in particle diameter manufactured by Daicel Chemical Industries, Ltd.). As a desorbing liquid, a solution prepared by mixing hexane with isopropanol in a ratio of 9 to 1 was fed at a rate of 27.9 ml/min.

As a result, an extract containing a strongly adsorbable isomer was obtained at a rate of 26.6 ml/min (concentration: 103.7 mg/ml), and a raffinate containing a weakly adsorbable isomer was obtained at a rate of 7.3 ml/min (concentration: 411.4 mg/ml).

COMPARATIVE EXAMPLE 1

The same feedstock was separated by a batch system using a single column containing the same packing as the one used in Example 1 to compare the throughput and the usage of desorbing liquid. The results are given in Table 1.

TABLE 1

| | Simulated moving bed system | Batch system |
|---|---|---|
| Throughput per unit time and unit packing (mg/ml-bed.min) | 2.4 | 0.084 |
| Usage of desorbing liquid (ml/mg feedstock) | 0.0093 | 2.0 |

It is apparent from Table 1 that the simulated moving bed system is superior to the batch system in both the throughput and the usage of desorbing liquid.

EXAMPLE 2

The same apparatus as that of Example 1 was used except that adsorbing chambers each having a diameter of 3 cm and a length of 100 cm were employed. Chiralcel OB having a particle diameter of from 30 to 50 μm was used as a packing, and α-PhEtOH (α-phenylethyl alcohol) was fed at a rate of 6 ml/min (total concentration of isomers: 1000 mg/ml). As a desorbing liquid, a solution prepared by mixing hexane with isopropanol in a ratio of 9 to 1 was fed at a rate of 61.4 ml/min. As a result, an extract containing a strongly adsorbable isomer was obtained at a rate of 58.5 ml/min (concentration: 28.6 mg/ml), and a raffinate containing a weakly adsorbable isomer was obtained at a rate of 8.9 ml/min (concentration: 336 mg/ml).

COMPARATIVE EXAMPLE 2

The same feedstock was separated by a batch system using a single column containing the same packing as the one used in Example 2 to compare the throughput and the usage of desorbing liquid. The results are given in Table 2.

TABLE 2

| | Simulated moving bed system | Batch system |
|---|---|---|
| Throughput per unit time and unit packing (mg/ml-bed.min) | 0.53 | 0.014 |
| Usage of desorbing liquid (ml/mg feedstock) | 0.02 | 4.5 |

It is apparent from Table 2 that the simulated moving bed system is superior to the batch system in both the throughput and the usage of desorbing liquid.

EXAMPLE 3

A solution of an optical isomer mixture containing 4200 ppm of racemic α-phenylethyl alcohol was fed at a rate of 5.9 ml/min into a simulated moving bed apparatus as shown in FIG. 2 which was comprised of 8 connected columns, as adsorbing chambers, each having an inside diameter of 2 cm and a length of 15 cm and containing a packing for use in the separation of an optical isomer (Chiralcel OB of 45 μm in particle diameter manufactured by Daicel Chemical Industries, Ltd.). As a desorbing liquid, a n-hexane/isopropanol (90/10 v/v %) mixture was fed at a rate of 24.2 ml/min. Each of the fluid feeding lines and draw-out lines was moved for a distance corresponding to one adsorbing chamber in the direction of fluid flow at given intervals of 3 minutes at 25° C. by automatic change-over operation of an eight-way rotary valve in order to perform continuous separation.

As a result, a raffinate containing a weakly adsorbable, optically active compound [(S)-(−)-α-phenylethyl alcohol] in a concentration of 1251.5 ppm at an optical purity of 99.9% e.e. or above was obtained at a rate of 9.7 ml/min. Moreover, an extract containing a strongly adsorbable, optically active compound [(R)-(+)-α-Phenylethyl alcohol] in a concentration of 613.4 ppm at an optical purity of 99.9% e.e. or above was obtained at a rate of 20.2 ml/min.

We claim:

1. A process for separating optical isomers in a simulated moving bed system, comprising introducing a solution containing an optical isomer mixture and a desorbing liquid into a packed bed containing an optical resolution packing therein and having front and rear ends thereof connected to each other endlessly via a recycle fluid passage to circulate a fluid unidirectionally and at the same time drawing out a solution containing one of the separated isomers and another solution containing the other isomer from the packed bed, wherein a port for introducing a desorbing liquid, an extract port for drawing out a solution containing a strongly adsorbable optical isomer a port for introducing a solution containing an optical isomer mixture, and a raffinate port for drawing out a solution containing a weakly adsorbable optical isomer are arranged in the packed bed in this order along the direction of fluid flow and the positions of these ports are successively moved in the direction of fluid flow in the packed bed intermittently.

*2. A process for separating optical isomers in a simulated moving bed system comprising the steps of introducing a solution containing an optical isomer mixture and a desorbing liquid into a packed bed containing an optical resolution packing therein and having front and rear ends thereof connected to each other endlessly via a recycle fluid passage to circulate a fluid unidirectionally and at the same time drawing out a solution containing one of the separated isomers and another solution containing the other isomer from the bed, a port for introducing a desorbing liquid, an extract port for drawing out a solution containing a strongly adsorbable optical isomer, a port for introducing a solution containing an optical isomer mixture and a raffinate port for drawing out a solution being arranged in the packed bed in this order along the direction of fluid flow and the positions of these sorts being successively moved in the direction of fluid flow in the packed bed intermittently, wherein the optical resolution packing is selected from the group consisting of an optically active high-molecular compound, an optically active high-molecular compound supported on a carrier and a low-molecular compound having an optical resolution capability supported on a carrier.*

*3. The process of claim 2, wherein the optical resolution packing is an optically active high-molecular compound.*

*4. The process of claim 3, wherein the optical resolution packing is an optically active high-molecular compound and the optically active high-molecular compound is a polysaccharide derivative.*

*5. The process of claim 2, wherein the optical resolution packing is a low-molecular compound having an optical resolution capability supported on a carrier.*

*6. The process of claim 5, wherein the optical resolution packing is a low-molecular compound having an optical resolution capability supported on a carrier and the low-molecular compound is a cyclodextrin derivative.*

*7. The process of claim 2, wherein the optical resolution packing is in the form of a particle.*

*8. The process of claim 7, wherein the optical resolution packing is in the form of a particle and has a particle size in the range of from 20 to 50 μm.*

*9. The process of claim 2, wherein the desorbing liquid comprises an organic solvent.*

*10. The process of claim 9, wherein the desorbing liquid comprises an organic solvent and the organic solvent is an alcohol and/or hydrocarbon.*

*11. The process of claim 10, wherein the desorbing liquid comprises an organic solvent, and the organic solvent is a mixture of an alcohol and a hydrocarbon.*

*12. The process of claim 11, wherein the desorbing liquid comprises an organic solvent, the organic solvent is a mixture of an alcohol and a hydrocarbon and the alcohol and hydrocarbon is isopropanol and hexane.*

*13. The process of claim 2, wherein the desorbing liquid comprises an aqueous solution containing a salt.*

*14. The process of claim 13, wherein the desorbing liquid comprises an aqueous solution containing a salt and the salt is copper sulfate or a perchlorate.*

* * * * *

UNITED STATES PATENT AND TRADEMARK OFFICE

CERTIFICATE OF CORRECTION

PATENT NO. : Re. 35 919

DATED : October 13, 1998

INVENTOR(S) : Akira YAMASHITA et al

It is certified that error appears in the above-identified patent and that said Letters Patent is hereby corrected as shown below:

Column 6, Line 46; change "these sorts being" to ---these ports being---.

Signed and Sealed this

Twenty-third Day of March, 1999

*Attest:*

Q. TODD DICKINSON

*Attesting Officer*

*Acting Commissioner of Patents and Trademarks*